United States Patent [19]

Lange

[11] Patent Number: 5,423,091
[45] Date of Patent: Jun. 13, 1995

[54] HEADBAND FOLLOWING A WEARER'S HAIRLINE

[75] Inventor: Susan M. Lange, Bloomington, Ill.

[73] Assignee: The TRAM Corporation, Bloomington, Ill.

[21] Appl. No.: 310,436

[22] Filed: Sep. 22, 1994

[51] Int. Cl.⁶ ............................................. A42C 5/02
[52] U.S. Cl. .................................... 2/181; 2/174; 2/DIG. 11
[58] Field of Search ............... 2/171, 174, 181, 207, 2/DIG. 11, 181.4; 4/521; 132/273, 274; 607/109

[56] References Cited

U.S. PATENT DOCUMENTS

| | | | |
|---|---|---|---|
| 2,640,198 | 6/1953 | Mullen | 2/174 |
| 4,223,407 | 9/1980 | Zappala | 2/174 |
| 4,394,782 | 7/1983 | Wasson | 2/181 |
| 5,038,412 | 8/1991 | Cionni | 2/181 |

*Primary Examiner*—Clifford D. Crowder
*Assistant Examiner*—Diana L. Biefeld
*Attorney, Agent, or Firm*—Philip L. Bateman

[57] ABSTRACT

A headband protects a woman from injury to the skin adjacent to the hairline during hair treatment. The headband is made of a flat, heat-insulating, moisture-absorbing material and its top edge is arcuate in the region covering the temples and forehead of the wearer, protruded in the region covering the ears, and substantially straight in the region covering the back of the neck, so that the headband follows the contour of the hairline when secured on the head of the wearer.

6 Claims, 1 Drawing Sheet

HEADBAND FOLLOWING A WEARER'S HAIRLINE

FIELD OF THE INVENTION

This invention relates to headbands. More particularly, this invention relates to headbands for protecting the skin adjacent the hairline during hair treatment.

BACKGROUND OF THE INVENTION

Women have treated the hair on their scalp for cosmetic and comfort purposes since prehistoric times. Men and children also treat their hair, although generally to a lesser degree than women. Many techniques are currently used to treat hair. For example, hair is cut to different lengths with a variety of instruments such as scissors, razors, and electric cutters. Hair is styled in various formations (commonly referred to as coiffures or hairdos), either with or without the addition of foreign objects. Hair is colored with bleaches and dyes. Hair is washed and/or conditioned with a variety of solutions to improve its appearance, texture, and manageability. Hair is straightened with chemical solutions or heated devices. And finally, hair is curled with chemical solutions, by wrapping wet hair around curling cylinders, or by wrapping hair around heated devices such as curling irons.

Hair above the surface of the skin is composed of hard, dead cells known as keratin. There are no nerve endings in these dead cells so there is no feeling from the hair shafts themselves when the hair is treated. In contrast, the skin, eyes, and ears are very sensitive to many of the chemical solutions used on the hair and to the cutting and heating devices. Accordingly, care must be taken during hair treatment to avoid injury to these organs. Nevertheless, injuries are common, both during self-treatment and during treatment by others, e.g., at a beauty salon. It would be very desirable if a protective device could be worn during hair treatment to avoid these injuries and yet still leave the hair completely exposed for treatment.

A number of headbands designed for protective purposes have been disclosed. For example, Smith, U.S. Pat. No. 5,033,122, issued Jul. 23, 1991, discloses a headband having a uniform width for protecting the eyes from perspiration forming on the forehead. The Smith headband does not follow the contours of the hairline so it leaves adjacent skin exposed and/or covers up a portion of the hair.

Cionni, U.S. Pat. No. 5,038,412, issued Aug. 13, 1991, discloses a headband for protecting the head and ears from the cold. The headband contains two insulated lobed sections for the ears.

Koritan, U.S. Pat. No. 5,046,195, issued Sep. 10, 1991, discloses a constant-width headband with a neck shield for protecting the wearer's neck from sunburn.

Manges, U.S. Pat. No. 4,656,671, issued Apr. 14, 1987, discloses a headband for protecting the wearer from eye injury when a hair solution is applied. The headband is a constant-width band of terry cloth with sections of Velcro at each end. A strip of elastic is sewn into the headband. The headband's top edge is straight so it does not follow the contour of the hairline.

Each of the above headbands leaves sensitive skin adjacent the hairline exposed and/or covers a portion of the hair. No headband has heretofore been disclosed which eliminates both of these drawbacks and which follows the contour of the hairline when secured on the head of the wearer.

SUMMARY OF THE INVENTION

The general object of this invention is to provide an improved headband. A more particular object is to provide a headband which protects a woman from injury to the skin adjacent to the hairline during hair treatment. Another more particular object is to provide a headband which leaves the hair completely exposed for treatment. Another more particular object is to provide a headband which can be removed after hair treatment without messing the hair.

I have invented an improved headband which protects a woman from injury to the skin adjacent to the hairline during hair treatment. The headband comprises a band of a flat material; the band having top and bottom edges and a width of about one-half to three inches; the band having means for securing the headband in position on the head of the wearer; the top edge of the band being arcuate in the region covering the temples and forehead of the wearer, being protruded in the region covering the ears, and being substantially straight in the region covering the back of the neck, so that the headband follows the contour of the hairline when secured on the head of the wearer.

This headband leaves the hair free for treatment, but provides protection to the skin and other organs close to the hairline. The headband is reusable, washable, easy to put on and take off, and extremely comfortable to wear. Wearing the headband greatly reduces the chances of injury to the skin, eyes, and ears.

DETAILED DESCRIPTION OF THE INVENTION

Figure 1:
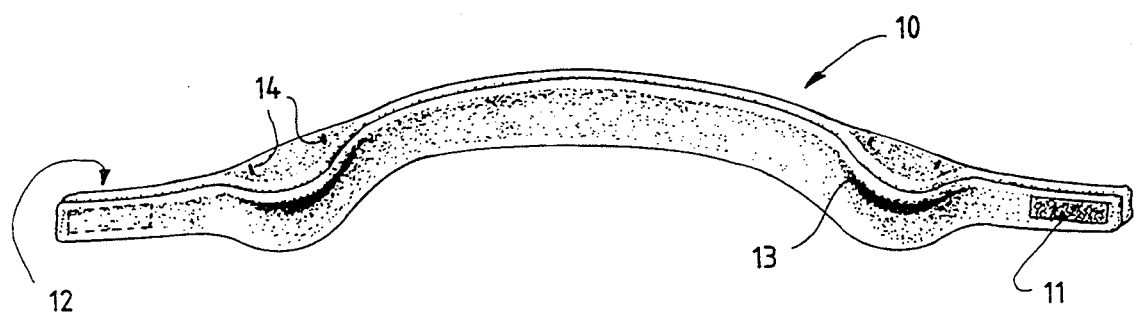
FIG. 1 is a front view of the inner surface of one embodiment of the headband of this invention.

This invention is best understood by reference to the drawings. In FIG. 1, a headband 10 is shown spread out flat with its inner surface (the one which faces inside toward the body) visible. The headband is shown in place on a woman's head in FIG. 2.

The headband is sized to go around the head of the wearer. For women, the length of the headband is generally about 16 to 24 inches. The headband is also useful for babies, children, and men and is sized accordingly. For babies, the length is generally about 12 to 20 inches; for children, about 14 to 22 inches; and for men, about 18 to 26 inches. The headband has an average width of about one-half to three inches. In general, headbands for babies and children have widths less than those for women and men. Widths less than about one-half inches offer less protection and widths greater than about three inches tend to block the vision of the wearer and to fold at the back of the neck. As shown in the drawings, the width of an individual headband varies from point to point because of its contoured shape.

Figure 2:
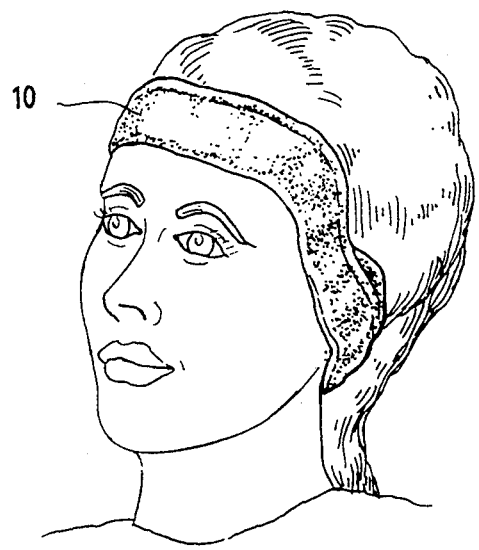
FIG. 2 is a perspective view of the headband shown in FIG. 1 in place on the head of a woman undergoing hair treatment.

The headband shown in FIGS. 1 and 2 is a strip in which the two ends are fastened together at the back of the wearer's head to form a closed band. Fastening at the back leaves a smooth, continuous surface at the front of the wearer's head where protection and comfort are most important. However, fastening at the front offers the advantage that it is easier to align the mating ends, especially if the headband is put on by the wearer herself. Any one of a variety of fastening devices are suitable, including hooks, buttons, ties, etc. The preferred fastening means are mating patches of Velcro hooks and loops. Velcro is very easy to fasten and unfasten and also can be overlapped varying amounts so that the length (circumference) of the headband can be adjusted for an optimal fit. In the embodiment shown in FIG. 1, a patch of Velcro hooks 11 on the inner surface mates with a patch of Velcro loops 12 on the outer surface (not seen in FIG. 1) of the opposite end. Alternatively, the headband is a continuous band of material which cannot be opened and closed. When the headband is continuous, it is preferred that the headband contain elastic so it can be held securely in place on the head. A drawback to a continuous headband is that removing the headband may mess the hair. In the case of short hair, this is generally not a problem. But if a woman with long hair has it styled in an elaborate manner, removing a continuous headband is a significant problem.

The headband is made of one, two, three, or more layers of material. If more than one layer of material is used, the layers may be of the same or different types of material depending on the desired properties and intended use of the headband. The exterior surfaces, especially the inner surface of the headband which contacts the skin, are preferably of a material which is non-irritating to the skin.

At least one of the layers of the headband is preferably made of a heat-insulating material so that it protects the skin from burns resulting from contact with hot curling irons and the like. Most of the common natural and synthetic fabrics are sufficiently heat-insulating that even relatively thin layers adequately protect the skin from curling iron burns. If superior heat-insulating properties are desired, the headband is preferably made with a layer of a material such as NOMEX, a silver-colored material widely used for ironing board covers and oven mitts; THINSULATE, an insulating material widely used in winter clothing; or the like.

The headband preferably contains at least one layer of material which is absorbent so that it prevents solutions on the hair from dripping down and into the eyes, ears, and face. If superior absorbency is desired, a highly effective headband is made of an inner layer of a material which "wicks" moisture away from the surface of the skin and transports it to an outer layer which absorbs it. An examples of such a wicking material is COOL-MAX fabric. Many athletic socks and underwear are made with this type of two-layer wicking-absorbing construction. Other highly-effective absorbents include cotton batting, foam, sponge, and terry cloth.

Each material used in the headband is preferably flame retardent so that the risk of fire is reduced. A large number of heat-insulating, absorbent, and flame-retardent materials are suitable for use in the headband. Suitable materials include natural fabrics such as cotton, cotton knits, terrycloth, linen, wool, and wool knits; synthetic fabrics such as polyester; and blends thereof such as cotton-polyester knits. Headbands made of such materials are generally washable and reusable. However, there are situations where inexpensive, disposable headbands are desirable. Materials similar to those used in paper toweling, disposable diapers, feminine protection pads and tampons, and surgical masks are well suited for such situations.

The headband has a shape which follows the contours of a woman's hairline. Children and many men have hairlines which are similar to women's. In contrast, a sizable percentage of middle-aged and older men exhibit male pattern baldness and have receding hairlines. A headband which follows the contours of a woman's hairline is generally satisfactory for most balding men. If desired, the headband shape can be modified to follow the contours of a severely balding man's hairline, but such a shape is not as practical for commercial purposes because of the limited number of persons on which it fits.

As seen in FIG. 1, the top edge of the headband in the region which covers the temples and forehead is arcuate in shape. This shape conforms closely to most women's hairlines when the headband is placed on the head. The center two or three inches of the arcuate region is, alternatively, made relatively straight if a more exact conformance to a straight hairline across the forehead is desired. The region which covers the ears is preferably protruded upward to cover the tops of the ears. Depending on the width of the headband, this region may also be protruded downward to cover the bottoms of the ears. The region which covers the back of the neck is substantially straight because the hairline between the bottoms of the ears is generally straight.

The bottom edge of the headband is preferably contoured to leave the eyes uncovered. During self treatment, the wearer often looks into a mirror so it is very desirable that the headband not block the vision. During treatment by others, this factor is of less importance, although most persons prefer to be able to see what is happening to their hair during treatment.

It is preferred that the headband contain ear pockets 13 which fold over the tops of the ears. The tops of the ears protrude and are very vulnerable to burns when the hair is being treated with a curling iron or the like. The ear pockets protect the entire upper surface of the ear. The ear pockets are separate pieces of material or, as shown in FIG. 1, extensions of the headband material. When the ear pockets are extensions, two small stitches 14 serve effectively to shape the pocket.

The use of the headband is simple: Place it on the head of the person about to undergo hair treatment and remove it when hair treatment is completed. The headband is especially useful when the hair is being curled with a hot curling iron. Not only does the headband prevent accidental burns, it actually enables the person using the curling iron to do a better job. With the headband in place, the curling iron can be rested against the headband as the hair along the hairline is cuffed. Without the headband, the cuffing iron must be suspended in mid-air and this instability often creates poor results.

I claim:

1. A headband to protect a person wearing it from injury to the skin adjacent the hairline during hair treatment;

the headband comprising a band of a flat material;

the headband being adapted to wrap around a wearer's head and having means for securing the headband in position on a wearer's head;

the headband having top and bottom edges and a width of about one-half to three inches;

the top edge of the headband being upwardly arcuate in a region covering a wearer's temples and forehead, being protruded upwardly in a region covering a wearer's ears, and being substantially straight in a region covering the back of a wearer's neck;

the bottom edge of the headband being substantially parallel to the top edge in the region covering a wearer's temples and forehead;

such that the headband is adapted to be worn with its entire top edge on top of, and following the contour of, a wearer's hairline leaving a wearer's eyes and hair exposed and covering a wearer's skin adjacent the hairline.

2. The headband of claim 1 wherein the band is a strip of material having means for fastening the ends of the band together to close the band.

3. The headband of claim 2 wherein the fastening means comprises hook and loop fasteners at the ends of the strip.

4. The headband of claim 1 wherein the headband comprises a layer of a heat-insulating material.

5. The headband of claim 1 wherein the headband comprises a layer of a absorbent material.

6. The headband of claim 1 wherein the headband contains two ear pockets which cover the tops of a wearer's ears when secured on the head of a wearer.

* * * * *